(12) United States Patent
Kano et al.

(10) Patent No.: US 12,121,512 B2
(45) Date of Patent: Oct. 22, 2024

(54) ANTI-FUNGAL AGENT

(71) Applicants: SEREN PHARMACEUTICALS INC., Tokyo (JP); NIHON UNIVERSITY, Tokyo (JP)

(72) Inventors: Rui Kano, Tokyo (JP); Osamu Ogawa, Tokyo (JP)

(73) Assignees: SEREN PHARMACEUTICALS INC. (JP); NIHON UNIVERSITY (JP)

( * ) Notice: Subject to any disclaimer, the term of this patent is extended or adjusted under 35 U.S.C. 154(b) by 120 days.

(21) Appl. No.: 17/602,139

(22) PCT Filed: Apr. 6, 2020

(86) PCT No.: PCT/JP2020/015471
§ 371 (c)(1),
(2) Date: Oct. 7, 2021

(87) PCT Pub. No.: WO2020/209215
PCT Pub. Date: Oct. 15, 2020

(65) Prior Publication Data
US 2022/0142987 A1     May 12, 2022

(30) Foreign Application Priority Data
Apr. 8, 2019    (JP) ................................ 2019-073394

(51) Int. Cl.
    A61K 31/427      (2006.01)
    A61P 31/10       (2006.01)

(52) U.S. Cl.
    CPC ............ *A61K 31/427* (2013.01); *A61P 31/10* (2018.01)

(58) Field of Classification Search
None
See application file for complete search history.

(56) References Cited

U.S. PATENT DOCUMENTS 5,648,372 A * 7/1997 Naito .................. C07D 409/06
                                             514/340

OTHER PUBLICATIONS

Kano R, Okubo M, Hasegawa A, Kamata H. Multi-azole-resistant strains of *Cryptococcus neoformans* var. *grubii* isolated from a FLZ-resistant strain by culturing in medium containing voriconazole. Med Mycol. Nov. 1, 2017;55(8):877-882. doi: 10.1093/mmy/myw101. PMID: 28927230. (Year: 2017).*
Yamaguchi H. Potential of Ravuconazole and its Prodrugs as the New OralTherapeutics for Onychomycosis. Med Mycol J. 2016;57(4):E93-E110. doi: 10.3314/mmj.16-00006. PMID: 27904057. (Year: 2016).*
Yamazumi et al., Antimicrob Agents Chemother. Oct. 2000;44(10):2883-2886 (Year: 2000).*
Kano et al., Med Mycol. Nov. 1, 2017;55(8):877-882 (Year: 2017).*
Yamaguchi et al., Med Mycol J. 2016 (Year: 2016).*
Yamaguchi, H., "Potential of Ravuconazole and its Prodrugs as the New Oral Therapeutics for Onychomycosis", Med. Mycol. J., 2016, pp. E93-E110, vol. 57E.
Kano, T. et al. Medical Mycology Journal, Feb. 2020, vol. 61., No. 1, pp. 11-13.
Yamazumi, T. et al. Antimicorbial Agents and Chemotherapy, Oct. 2000, pp. 2883-2886, vol. 44, No. 10.
Wang, Li et al, Chinese Journal of Antibiotics, 2002, vol. 27, No. 9, pp. 560-564.
Written Opinion of the International Searching Authority mailed Jun. 16, 2020 in International Application No. PCT/JP2020/015471.
Kano et al. "First Isolation of Azole-Resistant *Crptococcus neoformans* from Feline Cryptococcosis" Mar. 10, 2015, pp. 427-433, vol. 180.
Extended European Search Report in counterpart European Patent Application No. 20787150.0, mailed Dec. 23, 2022.
Kano, et al, "Antifungal Susceptibility of Clinical Isolates and Artificially Produced Multi-azole-resistant Strains of *Cryptococcus neoformans* (formerly: *Cryptococcus grubii*) to Ravuconazole." Med. Mycol J. vol. 61, 11-13, 2020.
Canton, et al. "Trends in antifungal susceptibility testing using CLSI reference and commercial methods". Expert Rev. Anti Infect. Ter. 7(1), 107-119, 2009.
Ana Espinel-Ingroff, et al. "Method for Antifungal Susceptibility Testing of the *Cryptococcus neoformans/C. gattii* Complex: Strengths and Limitations" Journal of Fungi, 2023, 9, 542 Retrieved from https://doi.org/10.3390/jof9050542.

* cited by examiner

*Primary Examiner* — Jeffrey S Lundgren
*Assistant Examiner* — Anthony Joseph Seitz
(74) *Attorney, Agent, or Firm* — Kim IP Law Group LLC

(57) ABSTRACT

An object of the present invention is to provide an antifungal agent which is effective against cryptococcosis. The present invention provides an antifungal agent comprising ravuconazole as an active ingredient, wherein the agent is administered to an animal suffering from cryptococcosis. Further, the present invention provides an antifungal agent comprising ravuconazole as an active ingredient, wherein the agent is administered to an animal suffering from *cryptococcus* that is resistant to triazole-based antifungal agents selected from the group consisting of fluconazole, itraconazole and voriconazole.

7 Claims, No Drawings

ANTI-FUNGAL AGENT

CROSS-REFERENCE TO RELATED APPLICATIONS

This application is a U.S. National Stage application under 35 U.S.C. § 371 of International Application No. PCT/JP2020/015471, filed on Apr. 6, 2020, which claims priority to JP2019-073394, filed Apr. 8, 2019, the disclosures of each of which hereby being incorporated by reference in their entirety for all purposes.

TECHNICAL FIELD

The present invention relates to an antifungal agent.

BACKGROUND ART

The present invention relates to antifungal agents. Specifically, the present invention relates to an antifungal agent which is effective for cryptococcosis.

Although many various fungi settle in the skin and body of animals including humans, they rarely do severe harm to animals. This is because the immunity of a host suppresses the growth of those indigenous fungi. However, when the immunity is reduced due to factors such as suffering from diseases that cause weakened immunity typified by acquired immunodeficiency syndrome (AIDS), using immunosuppressive agents for organ transplantation, deterioration of physical strength with aging or the like, indigenous fungi with low pathogenicity, whose growth is suppressed usually by the immunity, can multiply and resultantly cause diseases, which are called opportunistic infections. In other words, opportunistic infections are those in which a balance maintained between the host and the pathogen is disrupted due to a decrease in resistance in the host side, leading to the onset of diseases in the host. The opportunistic infections caused by fungi include, for example, candidiasis, cryptococcosis, and *pneumocystis* pneumonia (also referred to as *carinii* pneumonia).

Cryptococcosis is a fungal infection caused by a fungus *Cryptococcus neoformans* or *Cryptococcus gattii*, and is infected by inhaling yeast-like fungal cells. As a result, cryptococcosis usually affects nasal passages, respiratory tracts, and lungs. In addition, the infection can spread into tissues that cover the brain and spinal cord (meninges), causing meningitis. Further, it may invade from trauma and spread into tissues such as skin.

Although the fungus is present in all the world, cryptococcosis was relatively rare until the epidemic of AIDS began. Nowadays, however, it is the most common and potentially fatal fungal injection in AIDS patients. Most of pathogens for cryptococcosis in AIDS patients are *Cryptococcus neoformans*.

The pathogen for cryptococcal infection also infects people who have a lowered immune function other than AIDS patients. For example, the infection can also occur in people suffering from Hodgkin lymphoma or sarcoidosis, or people who are taking drugs that prevent rejection after organ transplantation or drugs that suppress the work of the immune system, such as corticosteroids (if used for a long period of time).

From the viewpoint of the serum type, *Cryptococcus neoformans* is further classified into type A (*Cryptococcus neoformans* var. *grubii* (called *Cryptococcus grubii*)), type D (*Cryptococcus neoformans* var. *neoformans* (called *Cryptococcus deneoformans*)), and type AD. Further, *Cryptococcus gattii* is further classified into type B and type C. In the temperate regions including Europe, America and the like in addition to Japan, *Cryptococcus neoformans* accounts for the majority of pathogen frequency in cryptococcosis patients other than AIDS patients. In the tropical regions, *Cryptococcus gattii* accounts for more than half. On the other hand, *Cryptococcus neoformans* accounts for most of the pathogen frequency in cryptococcosis patients suffering from AIDS, and especially in patients outside France, *Cryptococcus neoformans* var. *grubii*, the serotype A of *Cryptococcus neoformans*, accounts for 99% of the total. Even in Japan, *Cryptococcus neoformans* var. *grubii* infection accounts for most.

The incidence of patients of cryptococcosis in the general population is reported to be 0.209 per 100,000 per year. However, among AIDS patients, the annual incidence of patients is reported to be 2 to 4 per 1000, which is extremely high.

Animals other than humans can also suffer from cryptococcosis. In particular, cats are known to develop cryptococcosis. Spontaneous onset in healthy cats is also observed in some cases, but it is especially observed frequently in cats with weakened immunity due to feline immunodeficiency virus infection or feline leukemia virus infection. In Japan, *Cryptococcus neoformans* var. *grubii* is typically the pathogen for feline cryptococcosis. Cryptococcosis in non-human animals is thought to predominantly cause opportunistic infection. In mammals, birds, reptiles, etc. suffering from cryptococcosis, cold-like symptoms, pneumonia, encephalitis, miscarriage, endometritis, dermatitis, mastitis, etc. may occur. Birds are carriers of the pathogen *Cryptococcus neoformans*, and droppings of birds (especially pigeons) provide nutrients, hence, fungi are often found in soil contaminated with them.

On the other hand, the incidence rate of fungal infections has increased significantly over the last few decades. Many of these fungi have become resistant to first-line antifungal agents such as azoles and polyenes, hampering proper treatment and/or prevention of the diseases. Increased fungal infections and resistance to conventional therapeutic agents are world's important public health threats.

For the treatment of cryptococcosis, antifungal agents such as fluconazole (FLCZ), azole based antifungal agent, and the like are used. However, FLCZ resistant strains have been reported as isolates from human cryptococcosis patients. In addition, isolates of FLCZ-resistant *Cryptococcus neoformans* strains from cats suffering from cryptococcosis have been reported. Furthermore, it has been reported that if FLCZ-resistant strains are cultured in a medium containing voriconazole (VRCZ), which is an azole-based antifungal agent having a stronger antibacterial activity than FLCZ, multidrug-resistant strains against azole-based antifungal agents are easily separated. The emergence of multidrug-resistant bacteria against azole-based antifungal agents, which are used as first-line antifungal agents, is a major problem.

Ravuconazole is an azole-based antifungal agent similar to fluconazole and voriconazole, and exhibits an effective activity against a wide variety of fungi. It is reported to exhibit an excellent activity particularly to *Candida albicans* or *Cryptococcus neoformans* var. *neoformans* (Non-Patent Document 1: Yamaguchi, Med Mycol. J., vol. 57E, E73-E110, 2016). Ravuconazole is a triazole-based antifungal agent similar to fluconazole, but is not currently used as a pharmaceutical product.

CITATION LIST

Non-Patent Document

Non-Patent Document 1: Yamaguchi, Med. Mycol. J., vol. 57E, E73-E110, 2016

SUMMARY OF THE INVENTION

Technical Problem

An object of the present invention is to provide an antifungal agent which is effective against cryptococcosis.

Solution to Problem

The present inventors have intensively studied in order to solve the above problem and resultantly found that ravuconazole exhibits an effective antifungal action against the serotype A (*Cryptococcus neoformans* var. *grubii*) of *Cryptococcus neoformans*, which is one causative microorganism for cryptococcosis, and exhibits an antifungal action against *Cryptococcus neoformans* that has become multidrug-resistant, leading to completion of the present invention. The present invention includes the following aspects.

[1] An antifungal agent comprising ravuconazole as an active ingredient, wherein the agent is administered to an animal suffering from cryptococcosis.

[2] The antifungal agent according to the above [1], wherein the animal suffering from cryptococcosis is an animal infected with an immunodeficiency virus or a leukemia virus.

[3] The antifungal agent according to the above [1] or [2], wherein the animal is suffering from *Cryptococcus neoformans* var. *grubii*.

[4] The antifungal agent according to the above [3], wherein the *Cryptococcus neoformans* var. *grubii* is resistant to at least one selected from the group consisting of fluconazole, itraconazole and voriconazole.

[5] The antifungal agent according to the above [3], wherein the *Cryptococcus neoformans* var. *grubii* is resistant to at least two selected from the group consisting of fluconazole, itraconazole and voriconazole.

[6] The antifungal agent according to the above [1], wherein the cryptococcosis is a cryptococcosis caused by *cryptococcus* that is resistant to antifungal agents other than ravuconazole.

[7] The antifungal agent according to the above [6], wherein the antifungal agent other than ravuconazole is at least one antifungal agent selected from the group consisting of fluconazole, itraconazole and voriconazole.

[8] The antifungal agent according to any one of the above [1] to [7], wherein the animal is a human.

[9] The antifungal agent according to any one of the above [1] to [7], wherein the animal is a cat.

[10] An antifungal agent comprising as an active ingredient a prodrug of ravuconazole, wherein the agent is administered to an animal suffering from cryptococcosis.

[11] The antifungal agent according to the above [10], wherein the animal suffering from cryptococcosis is infected with an immunodeficiency virus or a leukemia virus.

[12] The antifungal agent according to the above [10] or [11], wherein the animal is suffering from *Cryptococcus neoformans* var. *grubii*.

[13] The antifungal agent according to the above [12], wherein the *Cryptococcus neoformans* var. *grubii* is resistant to at least one selected from the group consisting of fluconazole, itraconazole and voriconazole.

[14] The antifungal agent according to the above [12], wherein the *Cryptococcus neoformans* var. *grubii* is resistant to at least two selected from the group consisting of fluconazole, itraconazole and voriconazole.

[15] The antifungal agent according to the above [10], wherein the cryptococcosis is a cryptococcosis caused by *cryptococcus* that is resistant to antifungal agents other than ravuconazole.

[16] The antifungal agent according to the above [15], wherein the antifungal agent other than ravuconazole is at least one antifungal agent selected from the group consisting of fluconazole, itraconazole and voriconazole.

[17] The antifungal agent according to any one of the above [10] to [16], wherein the prodrug of ravuconazole is fosravuconazole.

[18] The antifungal agent according to any one of the above [10] to [17], wherein the animal is a human.

[19] The antifungal agent according to any one of the above [10] to [17], wherein the animal is a cat.

[20] An antifungal agent comprising ravuconazole as an active ingredient, wherein the agent is administered to an animal suffering from *cryptococcus* that is resistant to at least two triazole-based antifungal agents selected from the group consisting of fluconazole, itraconazole and voriconazole.

[21] The antifungal agent according to the above [20], wherein the *cryptococcus* is *Cryptococcus neoformans* var. *grubii*.

[22] An antifungal agent comprising as an active ingredient a prodrug of ravuconazole, wherein the agent is administered to an animal suffering from *cryptococcus* that is resistant to at least two triazole-based antifungal agents selected from the group consisting of fluconazole, itraconazole and voriconazole.

[23] The antifungal agent according to the above [22], wherein the *cryptococcus* is *Cryptococcus neoformans* var. *grubii*.

[24] The antifungal agent according to the above [22] or [23], wherein the prodrug of ravuconazole is fosravuconazole.

[25] The antifungal agent according to any one of the above [20] to [24], wherein the animal is a human.

[26] The antifungal agent according to any one of the above [20] to [24], wherein the animal is a cat.

[27] A method for treating an animal suffering from cryptococcosis, comprising administering to the animal a therapeutically effective amount of ravuconazole.

[28] The method according to the above [27], wherein the animal suffering from cryptococcosis is an animal infected with an immunodeficiency virus or a leukemia virus.

[29] The method according to the above [27] or [28], wherein the animal is suffering from *Cryptococcus neoformans* var. *grubii*.

[30] The method according to the above [29], wherein the *Cryptococcus neoformans* var. *grubii* is resistant to at least one selected from the group consisting of fluconazole, itraconazole and voriconazole.

[31] The method according to the above [27], wherein the cryptococcosis is a cryptococcosis caused by *cryptococcus* that is resistant to antifungal agents other than ravuconazole.

[32] The method according to the above [31], wherein the antifungal agent other than ravuconazole is at least one antifungal agent selected from the group consisting of fluconazole, itraconazole and voriconazole.

[33] The method according to any one of the above [27] to [32], wherein the animal is a human.

[34] The method according to any one of the above [27] to [32], wherein the animal is a cat.

[35] A method for treating an animal suffering from cryptococcosis, comprising administering to the animal a therapeutically effective amount of prodrug of ravuconazole.

[36] The method according to the above [35], wherein the animal suffering from cryptococcosis is an animal infected with an immunodeficiency virus or a leukemia virus.

[37] The method according to the above [35] or [36], wherein the animal is suffering from *Cryptococcus neoformans* var. *grubii*.

[38] The method according to the above [37], wherein the *Cryptococcus neoformans* var. *grubii* is resistant to at least one selected from the group consisting of fluconazole, itraconazole and voriconazole.

[39] The method according to the above [35], wherein the cryptococcosis is a cryptococcosis caused by *cryptococcus* that is resistant to antifungal agents other than ravuconazole.

[40] The method according to the above [39], wherein the antifungal agent other than ravuconazole is at least one antifungal agent selected from the group consisting of fluconazole, itraconazole and voriconazole.

[41] The method according to any one of the above [35] to [40], wherein the prodrug of ravuconazole is fosravuconazole.

[42] The method according to any one of the above [35] to [41], wherein the animal is a human.

[43] The method according to any one of the above [35] to [41], wherein the animal is a cat.

Advantageous Effect of the Invention

The present invention provides an antifungal agent which is effective against cryptococcosis.

DESCRIPTION OF EMBODIMENTS

Hereinafter, the present invention will be illustrated with reference to the exemplary embodiments along with preferred methods and materials which can be used in practice of the present invention. However, the present invention is not limited to the embodiments described below. Unless otherwise specified in the sentences, any technical terms and scientific terms used in the present specification have the same meaning as those generally understood by those of ordinary skill in the art to which the present invention belongs. Any materials and methods equivalent or similar to those described in the present specification can be used for practicing the present invention.

All publications and patents cited herein in connection with the present invention described herein are incorporated by reference, for example, as indicating methodology, materials, etc. that can be used in the present invention.

In the present specification, when the expression "X to Y" is used, it is used to include X as the lower limit and Y as the upper limit, or to include X as the upper limit and Y as the lower limit.

As used herein, the term "ravuconazole" in the context of an antifungal agent or therapeutic method is used to include all of ravuconazole, its pharmaceutically acceptable salts, hydrates and solvates. As used herein, the term "fosravuconazole" in the context of an antifungal agent or therapeutic method is used to include all of fosravuconazole, its pharmaceutically acceptable salts, hydrates and solvates.

One aspect of the present invention is an antifungal agent containing ravuconazole as an active ingredient, which is intended to be used for animals suffering from cryptococcosis.

Another aspect of the present invention is an antifungal agent containing ravuconazole as an active ingredient, which is intended to be used for an animal suffering from *cryptococcus* that has acquired multidrug resistance to an azole-based antifungal agent.

Another aspect of the present invention is an antifungal agent containing ravuconazole as an active ingredient, which is intended to be used for an animal infected with an immunodeficiency virus or a leukemia virus and further suffering from cryptococcosis.

Another aspect of the present invention is an antifungal agent containing a prodrug of ravuconazole, preferably fosravuconazole, as an active ingredient, which is intended to be used for an animal suffering from cryptococcosis.

Another aspect of the present invention is an antifungal agent containing a prodrug of ravuconazole, preferably fosravuconazole, as an active ingredient, which is intended to be used for an animal suffering from *cryptococcus* that has acquired multidrug resistance to an azole-based antifungal agent.

Another aspect of the present invention is an antifungal agent containing a prodrug of ravuconazole, preferably fosravuconazole, as an active ingredient, which is intended to be used for an animal infected with an immunodeficiency virus or a leukemia virus and further suffering from cryptococcosis.

Another aspect of the present invention is a method for treating an animal suffering from cryptococcosis, wherein a therapeutically effective amount of ravuconazole is administer to the animal.

Another aspect of the present invention is a method for treating an animal suffering from *cryptococcus* that has acquired multidrug resistance to an azole-based antifungal agent, wherein a therapeutically effective amount of ravuconazole is administer to the animal.

Another aspect of the present invention is a method for treating an animal infected with an immunodeficiency virus or a leukemia virus and further suffering from cryptococcosis, wherein a therapeutically effective amount of ravuconazole is administer to the animal.

Another aspect of the present invention is a method for treating an animal suffering from cryptococcosis, wherein a therapeutically effective amount of prodrug of ravuconazole, preferably fosravuconazole, is administer to the animal.

Another aspect of the present invention is a method for treating an animal suffering from *cryptococcus* that has acquired multidrug resistance to an azole-based antifungal agent, wherein a therapeutically effective amount of prodrug of ravuconazole, preferably fosravuconazole, is administer to the animal.

Another aspect of the present invention is a method for treating an animal infected with an immunodeficiency virus or a leukemia virus and further suffering from cryptococcosis, wherein a therapeutically effective amount of prodrug of ravuconazole, preferably fosravuconazole, is administer to the animal.

Ravuconazole has been reported as a compound showing an antifungal activity against various fungal pathogens including *Candida, Aspergillus*, and *Cryptococcus*. Ravuconazole is an azole-based antifungal compound having the following structural formula (I), and has a chemical structure similar to that of fluconazole.

[Chemical Formula 1]

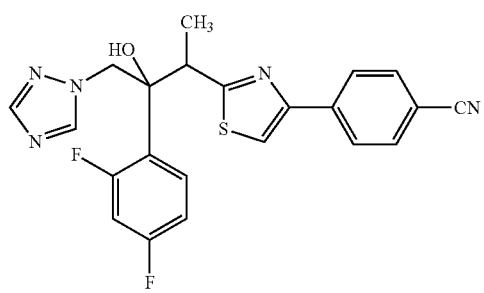

I

A method for producing ravuconazole is disclosed in, for example, Organic Process Research & Development 2009, 13, 716-728, and it can be produced with reference to such a disclosure. Such a disclosure constitutes a part of the present specification by reference. In the production, those skilled in the art can appropriately use techniques known in the art concerned without limitation.

Fosravuconazole is a compound having the following structural formula (II) in which the hydroxyl group of ravuconazole is substituted with a phosphomonooxymethyl ester.

[Chemical Formula 2]

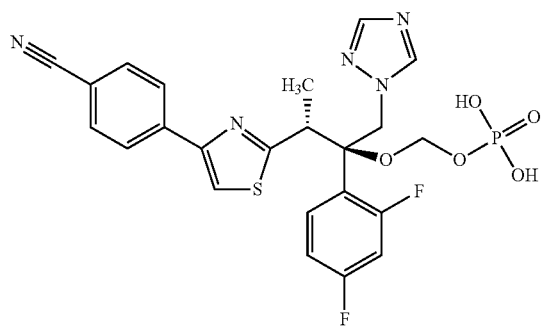

II

Fosravuconazole is a prodrug of ravuconazole that is rapidly converted to ravuconazole when administered to humans. The L-lysine ethanol adduct of fosravuconazole is currently marketed as a drug for nail tenea. Fosravuconazole can also be synthesized appropriately using techniques known in the art.

The ravuconazole contained in the antifungal agent of the present invention may be a pharmaceutically acceptable salt thereof. "Pharmaceutically acceptable salt" refers to any non-toxic salt formed from a compound represented by the formula (I). Suitable salts include, for example, but not limited to, inorganic acid salts such as hydrochloride, hydrobromide, hydroiodide, phosphate, hydrogen phosphate, sulfate, etc., organic acid salts such as acetate, trifluoroacetate, malate, succinate, tartrate, lactate, citrate, maleate, fumarate, sorbate, ascorbate, salicylate, phthalate, methyl sulfonate, trifluoromethyl sulfonate, benzene sulfonate, etc., inorganic salts such as ammonium salt, etc., alkali metal salts such as sodium salt, potassium salt, etc., alkaline earth metal salts such as calcium salt, magnesium salt, etc., salts of acidic groups such as carboxylic acid salt, etc., lower alkylamines such as methylamine, ethylamine, cyclohexylamine, etc., salts with organic bases such as substituted lower alkylamines such as diethanolamine, triethanolamine, etc., and amino acid salts such as glycine salt, lysine salt, arginine salt, ornithine salt, glutamic acid salt, aspartic acid salt, etc.

The ravuconazole contained in the antifungal agent of the present invention may also be a hydrous product such as a hydrate formed from a compound represented by the formula (I), or a solvate and the like. As used herein, the term "hydrate" means a compound or salt thereof that further contains a stoichiometric or non-stoichiometric amount of water bound by non-covalent intermolecular forces. As used herein, the term "solvate" means a compound or salt thereof that further comprises a stoichiometric or non-stoichiometric amount of solvent that is bound by non-covalent intermolecular forces. Preferred solvents are volatile, non-toxic and/or trace amounts of solvents that are acceptable for administration to humans. Examples thereof are, but not limited to, water, ethanol, and the like.

The fosravuconazole contained in the antifungal agent of the present invention may be a pharmaceutically acceptable salt thereof. "Pharmaceutically acceptable salt" refers to any non-toxic salt formed from a compound represented by the formula (II). Specifically, the above-mentioned salts described in relation to ravuconazole can be mentioned.

The fosravuconazole contained in the antifungal agent of the present invention may be a hydrous product such as a hydrate formed from a compound represented by the formula (II) or a solvate and the like. The hydrate and solvate have the same meaning as above. Preferred solvents are volatile, non-toxic and/or trace amounts of solvents that are acceptable for administration to humans, and include, but not limited to, water, ethanol and the like.

The fosravuconazole contained in the antifungal agent of the present invention as an active ingredient is preferably an L-lysine ethanol adduct of fosravuconazole.

The antifungal agent of the present invention may contain a prodrug of ravuconazole as an active ingredient. The "prodrug" of ravuconazole includes both "prodrug ester" and "prodrug ether". The "prodrug ester" includes esters and carbonates formed by reacting a hydroxyl of a compound represented by the formula (I) with any of an alkyl, an alkoxy, or an aryl-substituted acylating agent or a phosphorylating agent by a method known to those skilled in the art to generate an acetate, pivalate, methyl carbonate, benzoate, amino acid ester, phosphate, half acid ester (e.g., malonate, succinate, or glutarate) and the like. As used herein, the term "prodrug ether" includes both phosphate acetals and O-glucosides of compounds represented by the above-mentioned formula, which are produced using methods known to those skilled in the art.

The prodrug refers to a compound that is converted to the parent compound represented by the formula (I) in vivo, for example, by hydrolysis in blood.

The prodrug of ravuconazole contained in the antifungal agent of the present invention may be a pharmaceutically acceptable salt thereof. The prodrug of ravuconazole contained in the antifungal agent of the present invention may also be a hydrous product such as a hydrate, or a solvate and the like.

The prodrug contained in the antifungal agent of the present invention is preferably fosravuconazole, and more preferably a fosravuconazole-L-lysine ethanol adduct.

The antifungal agent of the present invention may include one or more pharmaceutically acceptable carriers and, as appropriate, other antifungal agents, in addition to any of ravuconazole or a prodrug of ravuconazole.

As used herein, the term "pharmaceutically acceptable carrier" includes any and all of solvents, dispersion media, coating agents, antioxidants, chelating agents, preservatives (e.g., antibacterial agents), surfactants, buffering agents, tonicity adjusting agents, absorption delaying agents, salts, drug stabilizers, excipients, diluents, binders, disintegrating agents, sweetening agents, fragrances, abundance agents, dyes, etc., and combinations thereof, as known to those skilled in the art. Unless any of the carriers is incompatible with the active ingredient in the present invention, it can be used in the antifungal agent (hereinafter, referred to as a composition in some cases) or the therapeutic method of the present invention.

As used herein, the term "therapeutically effective amount" refers to ravuconazole or a prodrug of ravuconazole (preferably, fosravuconazole) in an amount sufficient to produce a therapeutic effect, when administered to a mammal in need of treatment. The therapeutically effective amount varies depending on the subject and the disease symptoms to be treated, the weight and age of the subject, the severity of the disease symptoms, the administration method, and the like, and can be easily determined by those skilled in the art.

As used herein, the term "subject" is an animal in need of treatment and includes mammals, birds and fish. Typically, the animal is a mammal. For example, it refers to a primates (e.g., a human), a cat, a dog, a cow, a sheep, a goat, a horse, a rabbit, a rat, mouse, a koala, and the like. In certain embodiments, the animal as the subject is preferably a human, a cat or a dog, and more preferably a human or a cat.

The subject to which the antifungal agent of the present invention is administered is an animal suffering from cryptococcosis. Preferably, it is an animal suffering from cryptococcosis and having an immune system function lowered due to infection with an immunodeficiency virus or a leukemia virus or for other reasons. More preferably, it is an animal suffering from *Cryptococcus neoformans* var. *grubii* as a causative pathogen for cryptococcosis.

The antifungal agent of the present invention containing any of ravuconazole (the formula (I)) or a prodrug of ravuconazole (e.g., fosravuconazole (the formula (II))) can be formulated according to known methods for formulating pharmaceutical compositions. Representative pharmaceutical compositions may include the pharmaceutically acceptable carriers described above. The use of these carriers is well known in the art. Further, a method for preparing a pharmaceutical composition containing an active ingredient is well known in the art.

The composition of the present invention can be formulated to suit a specific route of administration according to the intended use. Routes of administration include, but are not limited to, oral, parenteral, intravenous, intradermal, subcutaneous, transdermal, inhalation, topical, transmucosal, or rectal administration. The compositions of the present invention can be formulated in solid or liquid form. The solid form includes, but are not limited to, tablets, capsules, pills, granules, powders, or suppositories. The liquid form includes, but are not limited to, solutions, suspensions, or emulsions. The composition of the present invention is preferably administered orally.

The composition of the present invention formulated for oral administration may be either a liquid composition or a solid composition. For liquid formulations, a composition can be prepared using liquid carriers such as water, glycols, oils, alcohols and analogous materials. For solid formulations such as tablets and capsules, a composition can be prepared using solid carries such as starches, sugars, kaolin, ethyl cellulose, calcium carbonate and sodium carbonate, calcium phosphate, talc, lactose and the like, while generally containing a binding agent, a disintegrating agent and analogous materials together with a lubricant such as calcium stearate. Tablets and capsules are the most advantageous oral dosage forms because they are easy to administer. For ease of administration and dosage uniformity, it is particularly advantageous to formulate the composition in unit dosage form. The composition in unit dosage form constitutes one aspect of the invention.

The composition may be prepared for injection, and can take a form of solution, emulsion or suspension in an oily or aqueous vehicle such as 0.85% sodium chloride or 5% dextrose in water. It can also contain formulating agents such as suspending agents, stabilizers and/or dispersants. Buffering agents and additives (saline or glucose, etc.) can be added to make the solution isotonic. For drip intravenous administration, the compounds can also be dissolved in alcohol/propylene glycol or polyethylene glycol.

These compositions can also be provided in unit dosage forms, preferably in ampoules or in multi-dose containers, with preservatives added. Alternatively, the active ingredient can be in powder form to reconstitute with a suitable vehicle prior to administration.

Oral administration or intravenous administration is usually used for administration of the composition of the present invention. If the composition of the present invention is used for the treatment of cryptococcosis, when it is desirable to directly treat the lungs and bronchi, an inhalation method is preferred when there is no complication of infection to the central nervous system such as meningitis. For administration by inhalation, the compound of the present invention delivered in aerosol particles using, for example, a nebulizer. A preferred delivery system for inhalation is a metered dose inhalation (MDI) aerosol. Oral or intravenous administration including liquid preparations is considered if the patient has or is likely to have an infection of the central nervous system such as meningitis. Liquid preparations are preferably used for administration of the compositions of the present invention in the treatment of cryptococcosis.

The dose of the compound in the composition of the present invention is appropriately selected depending on the type of disease, the symptom of the subject to be administered, the age, the administration route and the like. In the case of administration to humans, for example, the oral preparation may be administered, but not limited to, at a proportion of usually 10 to 5000 mg, preferably 20 to 2000 mg, more preferably 50 to 500 mg, and still more preferably 100 to 200 mg per day, once to twice per day, for several weeks to several months, in some cases, six months to 1 year, continuously or intermittently. In the case of administration to cats, for example, it may be administered, but not limited to, at a proportion of usually 2 to 1000 mg, preferably 10 to 100 mg, and more preferably 20 to 40 mg per day, once to twice per day, for several weeks to several months, in some cases, six months to 1 year, continuously or intermittently.

The composition of the present invention may also contain other antifungal agents in addition to ravuconazole or fosravuconazole. Other antifungal agents include, but are not limited to, natamycin, rimocidin, nystatin, amphotericin B, candicine, hamycin, perimycin, miconazole, ketoconazole, clotrimazole, econazole, omoconazole, bifonazole, butoconazole, fenticonazole, isoconazole, oxiconazole, sertaconazole, sulconazole, tioconazole, fluconazole, fosfluconazole, itraconazole, isavuconazole, posaconazole, voriconazole, terconazole, albaconazole, abafungin, terbinafine, naftifine, butenafine, amorolfine, anidulafungin, caspofungin, micafungin, ciclopirox, tolnaftate, or flucytosine. Thus, the composition of the present invention contains a combination (combination agent) of the two or more active ingredients including other antifungal agents, in addition to ravuconazole or a prodrug of ravuconazole (preferably, fosravuconazole).

The compositions of the present invention can also be administered concomitantly with other antifungal agents for concomitant therapy. Concomitant administration includes sequential, simultaneous or parallel administration of the two drugs. As other antifungal agents that can be administered concomitantly, the antifungal agents can be used without limitation.

Additionally, the present invention includes a method for treating cryptococcosis, comprising administering a therapeutically effective amount of ravuconazole or a prodrug of ravuconazole (preferably, fosravuconazole) to a patient.

Further, the present invention includes a method for treating cryptococcosis, comprising administering to a patient in combination with other known antifungal agents (concomitant use). Other antifungal agents include those exemplified with respect to the combination agent described above.

EXAMPLES

Hereinafter, the present invention will be specifically described with reference to Examples, but the present invention is not limited to the following Examples.

*Cryptococcus neoformans* clinical isolates and multidrug-resistant strains isolated from fluconazole (FLCZ) resistant strains were used to test their sensitivity to ravuconazole.

(Example 1) Separation of Isolate and Resistant Strain

Six isolates of *cryptococcus* were obtained from skin-infected cats and five from systemically infected cats, for a total of 11 strains. One strain of cat skin *cryptococcus* and one strain of cat systemic *cryptococcus* were fluconazole-resistant.

Three isolates of *cryptococcus* were acquired from skin-infected humans.

All of the above-acquired isolates were *Cryptococcus neoformans* var. *grubii* strains (type A).

Further, as described below, 3 multidrug-resistant strains resistant to fluconazole (FLCZ) and voriconazole (VRCZ) as azole-based antifungal agents were acquired.

Clinically separated fluconazole (FLCZ) resistant *Cryptococcus neoformans* cells (2.3×10$^5$) were inoculated on Sabouraud glucose agar medium containing 3 μg/ml of voriconazole (VRCZ), and cultured at room temperature for 7 days. Thereafter, 12 colonies generated on the plate were inoculated on Sabouraud glucose agar medium containing 5 μg/ml of VRCZ. This was cultured at room temperature for 10 days, and the obtained colonies were further subcultured, to obtain 3 azole-based multidrug-resistant strains.

(Example 2) Sensitivity to Each Azole-Based Drug

The strains obtained in Example 1 were maintained on Sabouraud glucose agar medium until the test of sensitivity to antifungal compounds.

Sensitivity to ravuconazole (RVCZ) was determined according to the CLSI M27-A3 guideline using broth microdilution assay. The minimum inhibitory concentration (MIC) was measured after culturing at 35° C. for 72 hours. MIC was defined as the lowest concentration that induces significant inhibition of growth (inhibition of about 50% or more).

Sensitivity to fluconazole (FLCZ), itraconazole (ITCZ) and voriconazole (VRCZ) was evaluated using the E-test. The E-test was performed using RPMI-1640 agar medium placed in a 90 mm Petri dish according to the E-test Technical Guide 10 (AB BIODISK, Sweden). E-test gradient strips were purchased from AB BIODISK. The MICs for FLCZ, ITCZ and VRCZ were determined after culturing at 35° C. for 72 hours. Each isolate was tested twice at shifted times, and each test included twice measurements.

The test results are shown in Table 1.

TABLE 1

| Strain Number | Origin | FLCZ[a] | ITCZ[a] | VRCZ[a] | RVCZ[b] |
|---|---|---|---|---|---|
| No. 1 | Feline cutaneous cryptococcosis | 3 | 0.047 | 0.008 | 0.03125 |
| No. 2 | Feline systemic cryptococcosis | <0.016 | 0.002 | <0.002 | 0.03125 |
| No. 3 | Feline systemic cryptococcosis | 6 | 0.23 | 0.032 | 0.03125 |
| No. 4 | Feline cutaneous cryptococcosis | 16 | 0.018 | 0.064 | 0.0625 |
| No. 5 | Feline cutaneous cryptococcosis | 32 | 0.5 | 0.125 | 0.0625 |
| No. 6 | Feline systemic cryptococcosis | 2 | 0.064 | 0.047 | 0.125 |
| No. 7 | Feline systemic cryptococcosis | 1.5 | 0.38 | 0.032 | 0.0625 |
| No. 8[c] | Feline systemic cryptococcosis | >256 | 0.25 | 0.094 | 0.125 |
| No. 9 | Feline systemic cryptococcosis | 1.5 | 0.23 | 0.012 | 0.03125 |
| No. 10 | Feline cutaneous cryptococcosis | 14 | 0.75 | 0.023 | 0.125 |
| No. 11 | Human cutaneous cryptococcosis | 1.5 | 0.19 | 0.003 | 0.03125 |
| No. 12 | Human cutaneous cryptococcosis | 1.5 | 0.125 | 0.006 | 0.03125 |
| No. 13 | Human cutaneous cryptococcosis | 0.75 | 0.125 | 0.003 | 0.03125 |
| No. 14[c] | Feline cutaneous cryptococcosis | 128 | 0.38 | 0.023 | 0.125 |
| No. 15 | Multi-azole resistance strain | >256 | >32 | 12 | 0.5 |
| No. 16 | Multi-azole resistance strain | >256 | >32 | 8 | 0.5 |
| No. 17 | Multi-azole resistance strain | >256 | >32 | 6 | 0.25 |

[a]MICs were assayed by the E-test.
[b]MICs were assayed by the CLSI M27-A3.
[c]FLCZ resistant strain.
FLCZ: fluconazole, ITCZ: itraconazole, VRCZ: voriconazole, RVCZ: ravuconazole The average MIC of the 14 isolates (Nos. 1-14) was 17.313 mg/L (range: <0.016-128 mg/L) for fluconazole, 0.235 mg/L (range: <0.002-0.75 mg/L)) for itraconazole, 0.036 mg/L (range: <0.002-0.125 mg/L) for voriconazole, and 0.0376 mg/L (range: <0.003125-0.25 mg/L) for ravuconazole. Ravuconazole showed remarkable results compared to other azole-based antifungal compounds.

On the other hand, the MIC of the azole-based multidrug-resistant strains (Nos. 15-17) was >256 mg/L for fluconazole, >32 mg/L for itraconazole, 6-12 mg/L for voriconazole, and 0.25-0.5 mg/L for ravuconazole, that is, ravuconazole showed a remarkable effect.

CLSI M27-A3 test and E-test MIC assay were performed using *Candida parapsilosis* ATCC 22019 and *Candida kruzei* ATCC 6258 purchased from ATCC as controls. As a result, a high correlation was observed between the MIC results of the azole-based drugs obtained in the CLSI M27-A3 test and the E-test, so the results of both were compared.

The foregoing merely illustrates objects and subjects of the present invention, and is not intended to be limiting the accompanying Claims. Without departing from the accompanying Claims, various modifications and alterations to the described embodiments will be apparent to those skilled in the art in view of the teachings herein.

INDUSTRIAL APPLICABILITY

The antifungal agent containing ravuconazole provided by the present invention is useful as a therapeutic agent for cryptococcosis.

The invention claimed is:

1. A method for treating an animal suffering from cryptococcosis, comprising administering to the animal a therapeutically effective amount of a compound selected from the group consisting of ravuconazole, a prodrug of ravuconazole, and pharmaceutically acceptable salts, hydrates and solvates thereof, wherein the animal suffering from cryptococcosis is an animal suffering from a *Cryptococcus* resistant to at least two antifungal agent selected from the group consisting of fluconazole, itraconazole and voriconazole.

2. The method according to claim 1, wherein the *Cryptococcus* is *Cryptococcus neoformans* var. *grubii*.

3. The method according to claim 1, wherein the animal suffering from cryptococcosis is an animal infected with an immunodeficiency virus or a leukemia virus.

4. The method according to claim 1, wherein the animal is a human.

5. The method according to claim 1, wherein the animal is a cat.

6. The method according to claim 1, wherein the prodrug of ravuconazole is fosravuconazole.

7. The method according to claim 1, wherein the compound is L-lysine ethanol adduct of fosravuconazole.

* * * * *